United States Patent
Galie et al.

(10) Patent No.: US 10,280,543 B2
(45) Date of Patent: May 7, 2019

(54) METHODS FOR MAKING ZONED APERTURED WEBS

(71) Applicant: The Procter & Gamble Company, Cincinnati, OH (US)

(72) Inventors: Theresa Lynn Galie, Cincinnati, OH (US); James Terry Knapmeyer, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 573 days.

(21) Appl. No.: 14/247,276

(22) Filed: Apr. 8, 2014

(65) Prior Publication Data
US 2015/0284892 A1 Oct. 8, 2015

(51) Int. Cl.
*D06C 3/06* (2006.01)
*D04H 1/54* (2012.01)
(Continued)

(52) U.S. Cl.
CPC .......... *D06C 3/06* (2013.01); *A61F 13/15707* (2013.01); *A61F 13/15731* (2013.01); *A61F 13/15804* (2013.01); *A61F 13/5122* (2013.01); *A61F 13/5126* (2013.01); *B26F 1/00* (2013.01); *D04H 1/54* (2013.01); *D04H 1/5405* (2013.01); *D04H 1/558* (2013.01); *D06C 7/00* (2013.01); *D06C 19/00* (2013.01); *D10B 2401/10* (2013.01); *D10B 2403/01* (2013.01)

(58) Field of Classification Search
CPC ................ A61F 13/512; A61F 13/5126; A61F 13/51305
See application file for complete search history.

(56) References Cited

U.S. PATENT DOCUMENTS

| | | | |
|---|---|---|---|
| 5,354,400 A | | 10/1994 | Lavash et al. |
| 5,389,173 A | * | 2/1995 | Merkatoris ....... A61F 13/15609 156/161 |

(Continued)

FOREIGN PATENT DOCUMENTS

EP     1004412     5/2000

OTHER PUBLICATIONS

International Search Report and Written Opinion, PCT/2015/023551, dated Jul. 27, 2015.

*Primary Examiner* — Jeffry H Aftergut
*Assistant Examiner* — Jaeyun Lee
(74) *Attorney, Agent, or Firm* — Daniel S. Albrecht

(57) ABSTRACT

A method for making a zoned apertured nonwoven web comprises providing an unapertured nonwoven web having a first plurality of weakened locations in a first pattern in a first zone and a second plurality of weakened locations in a second pattern in a second zone. The method comprises applying a substantially cross machine directional tensioning force to the nonwoven web to cause the nonwoven web to rupture at some of the first and second pluralities of weakened locations. The applying step creates a plurality of first apertures in the nonwoven web coincident with the some of the first plurality of weakened locations and a plurality of second apertures in the nonwoven web coincident with the some of the second plurality of weakened locations. The cross machine directional width of the nonwoven web after the applying step is substantially the same in the first zone and the second zone.

18 Claims, 15 Drawing Sheets

(51) Int. Cl.
*D04H 1/558* (2012.01)
*D06C 7/00* (2006.01)
*D06C 19/00* (2006.01)
*A61F 13/512* (2006.01)
*A61F 13/15* (2006.01)
*B26F 1/00* (2006.01)

(56) References Cited

U.S. PATENT DOCUMENTS

| | | | |
|---|---|---|---|
| 5,628,097 A | 5/1997 | Benson et al. | |
| 5,658,639 A | 8/1997 | Curro et al. | |
| 5,714,107 A * | 2/1998 | Levy | D04H 1/54 |
| | | | 264/146 |
| 5,916,661 A | 6/1999 | Benson et al. | |
| 5,990,337 A | 11/1999 | Kleiner | |
| 6,498,284 B1 | 12/2002 | Roe | |
| 6,632,504 B1 | 10/2003 | Gillespie et al. | |
| 6,811,239 B1 | 11/2004 | Salacz | |
| 7,589,249 B2 | 9/2009 | Gubernick et al. | |
| 8,022,267 B2 | 9/2011 | Hellström et al. | |
| 8,158,043 B2 | 4/2012 | Gibson et al. | |
| 8,241,543 B2 | 8/2012 | O'Donnell et al. | |
| 8,440,587 B2 | 5/2013 | Arora et al. | |
| 2003/0021951 A1 | 1/2003 | Desai et al. | |
| 2004/0265544 A1 | 12/2004 | Di Salvo et al. | |
| 2005/0116976 A1 | 6/2005 | Salacz et al. | |
| 2005/0119631 A1 | 6/2005 | Giloh et al. | |
| 2006/0107505 A1 | 5/2006 | Desai et al. | |
| 2008/0208153 A1 | 8/2008 | Oetjen et al. | |
| 2009/0030390 A1 * | 1/2009 | Hammons | A61F 13/512 |
| | | | 604/367 |
| 2010/0036346 A1 | 2/2010 | Hammons et al. | |
| 2011/0094669 A1 | 4/2011 | Oetjen | |
| 2011/0094674 A1 | 4/2011 | Oetjen | |
| 2012/0049404 A1 | 3/2012 | Gibson et al. | |
| 2012/0273990 A1 | 11/2012 | O'Donnell et al. | |
| 2012/0273997 A1 | 11/2012 | Stone et al. | |
| 2012/0276337 A1 * | 11/2012 | Curro | B29C 55/18 |
| | | | 428/156 |
| 2012/0276341 A1 | 11/2012 | Lake et al. | |
| 2013/0158497 A1 | 6/2013 | Yamaguchi et al. | |
| 2014/0120323 A1 | 5/2014 | Lake et al. | |

* cited by examiner

METHODS FOR MAKING ZONED APERTURED WEBS

FIELD

The present disclosure is generally directed to methods for making zoned apertured webs and, is more particularly related to, methods for making zoned apertured nonwoven webs useful in absorbent articles and other articles of commerce. The present disclosure is also directed to nonwoven webs or topsheets for absorbent articles.

BACKGROUND

Webs, such as nonwoven webs, have many uses, such as in cleaning sheets, medical applications, wipes, absorbent articles, topsheets for absorbent articles, and other articles of commerce or consumer products. In some instances, it may be desirable to have a plurality of apertures through the webs in various locations, for example, to allow fluids or gases to more easily pass through the webs. These apertures may be formed using any suitable process. Typically, the apertures are the same in size, pattern, and orientation throughout the webs to provide the webs with uniform or substantially uniform web widths in a cross machine direction. As an example, a web used as a topsheet of an absorbent article may have the same pattern, size, and orientation of apertures on first and second sides of a lateral axis or a substantially laterally extending structural separator. It has typically been desired to have the same aperture areas, sizes, patterns, and orientations throughout a web owing to web processing considerations during manufacture of the various webs or during the manufacture of other consumers products (e.g., absorbent articles) incorporating the webs. One main consideration of web processing is that zones of the web in the cross machine direction have a constant width or a substantially constant width in the cross machine direction. If the webs, such as topsheets, do not have constant, or substantially constant, cross machine directional widths, processing problems, such as the topsheet coming apart from the leg cuffs thereby potentially causing leakage in an absorbent article, and improper cross machine directional spreading which may cause the aperture to not "open" correctly, may occur. In view of the fact that these webs are typically made at very high speeds (e.g., 1200-2000 ft/min), any significant web cross machine directional width fluctuations can lead to many processing and performance issues. To alleviate such web processing and performance problems, web manufacturers typically create webs with the same pattern, size, and orientation of apertures in all zones of the web (the zones being in the machine direction). The present disclosure, however, teaches how to process webs having machine direction zones with different effective aperture areas, sizes, patterns, and/or orientations while still maintaining a constant, or substantially constant, cross machine directional widths in the zones of the webs, thereby alleviating performance and processing issues with the webs.

SUMMARY

In one form, the present disclosure is directed, in part, to a method for making a zoned apertured nonwoven web. The method may comprise advancing the nonwoven web in a machine direction, weakening the nonwoven web at a plurality of first locations in a first zone of the nonwoven web to create a first plurality of weakened locations that are situated in a first pattern, and weakening the nonwoven web at a plurality of second locations in a second zone of the nonwoven web to create a second plurality of weakened locations that are situated in a second pattern that is different than the first pattern. The first zone is positioned further upstream than the second zone relative to the machine direction. The method may comprise incrementally stretching the nonwoven web to locally extend portions of the nonwoven web in a direction substantially parallel to a cross machine direction to cause the nonwoven web to rupture at some of the first and second pluralities of weakened locations in the first and second zones, and applying a substantially cross machine directional tensioning force to the nonwoven web to cause the nonwoven web to further define at the some of the first and second pluralities of weakened locations in the first and second zones. The applying step may create a plurality of first apertures in the nonwoven web coincident with the some of the first plurality of weakened locations in the first zone, and a plurality of second apertures in the nonwoven web coincident with the some of the second plurality of weakened locations in the second zone. The cross directional width of the nonwoven web after the applying step is substantially the same in the first zone and the second zone.

In another form, the present disclosure is directed, in part, to a method for making a zoned apertured nonwoven web. The method may comprise providing an unapertured nonwoven web comprising a first plurality of weakened locations that are situated in a first pattern in a first zone and a second plurality of weakened locations that are situated in a second, different pattern in a second zone. The method may comprise advancing the nonwoven web in a machine direction such that the first zone is positioned further upstream relative to the second zone in the machine direction and incrementally stretching the nonwoven web to locally extend portions of the nonwoven web in a direction substantially parallel to a cross machine direct to cause the nonwoven web to rupture at some of the first and second pluralities of weakened locations in the first and second zones. The method may comprise applying a substantially cross machine directional tensioning force to the nonwoven web to cause the nonwoven web to further define at the some of the first and second pluralities of weakened locations in the first and second zones. The applying step may create a plurality of first apertures in the nonwoven web coincident with the some of the first plurality of weakened locations in the first zone and a plurality of second apertures in the nonwoven web coincident with the some of the second plurality of weakened locations in the second zone. The cross machine directional width of the nonwoven web after the applying step is substantially the same in the first zone and the second zone.

In still another form, the present disclosure is directed, in part, to a method for making a zoned apertured nonwoven web. The method may comprise providing a nonwoven web comprising a first plurality of weakened locations that are situated in a first pattern in a first zone and a second plurality of weakened locations that are situated in a second, different pattern in a second zone. The method may comprise advancing the nonwoven web in a machine direction such that the first zone is positioned further upstream than the second zone relative to the machine direction and applying a substantially cross machine directional tensioning force to the nonwoven web to cause the nonwoven web to rupture at some of the first and second pluralities of weakened locations in the first and second zones. The applying step may create a plurality of first apertures in the nonwoven web coincident with the some of the first plurality of weakened locations in the first zone and a plurality of second apertures in the nonwoven web coincident with the some of the second plurality of weakened locations in the second zone. The plurality of first apertures each have an effective aperture area that is different than an effective aperture area of the plurality of second apertures. The cross machine directional width of the nonwoven web after the applying step is substantially the same in the first zone and the second zone.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting forms of the disclosure taken in conjunction with the accompanying drawings, wherein.

DETAILED DESCRIPTION

Figure 1:
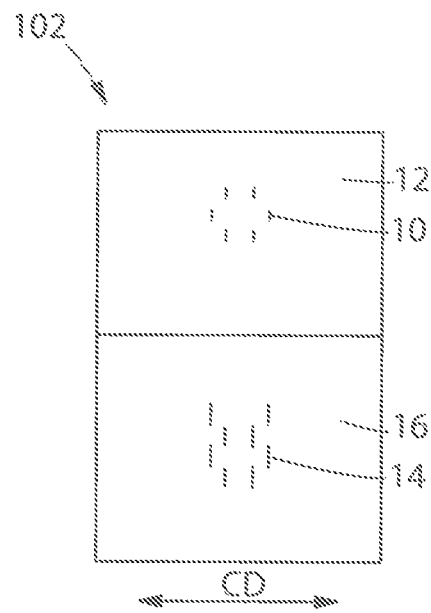
FIG. 1 is a schematic representation of an example web having a first zone comprising a first plurality of weakened locations and a second zone comprising a second plurality of weakened locations in accordance with the present disclosure.

Various non-limiting forms of the present disclosure will now be described to provide an overall understanding of the principles of the structure, function, manufacture, and use of the methods for making zoned apertured webs disclosed herein. One or more examples of these non-limiting forms are illustrated in the accompanying drawings. Those of ordinary skill in the art will understand that the methods for making zoned apertured webs described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

DEFINITIONS

As used herein, the term "absorbent article" refers to disposable devices such as infant, child, or adult incontinence diapers, training pants, incontinence pants, sanitary napkins, and the like which are placed against or in proximity to the body of the wearer to absorb and contain the various exudates discharged from the body (e.g., menses and urine). Typically, these articles comprise a topsheet, backsheet, an absorbent core, optionally an acquisition system (which may be comprised of one or several layers), and typically other components, with the absorbent core normally placed at least partially between the backsheet and the acquisition system or between the topsheet and the backsheet. The absorbent articles may take on any suitable configuration.

As used herein, the term "nonwoven web" means a manufactured sheet, web, or batt of directionally or randomly orientated fibers, bonded by friction, and/or cohesion, and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers may have diameters ranging from less than about 0.001 mm to more than about 0.2 mm and may come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding, and airlaying. The basis weight of nonwoven webs is usually expressed in grams per square meter (g/m² or gsm). Bicomponent fibers, or any other suitable fibers, may also be used in forming the nonwoven webs.

As used herein, the terms "joined" or "bonded" or "attached" encompass configurations whereby an element is directly secured to another element by affixing the element directly to the other element, and configurations whereby an element is indirectly secured to another element by affixing the element to intermediate member(s) which in turn are affixed to the other element.

As used herein, the term "extensible" refers to any material which, upon application of a biasing force, is elongatable, at least about 50% without offering a significant resistance force (less than 10 g/cm) or experiencing catastrophic failure. Catastrophic failure includes substantial tearing, fracturing, rupturing, or other failure in tension such that, if tested in a standard tensile tester, the failure would result in a sudden significant reduction in measured tensile force. As used herein, the term "highly extensible" refers to any material which, upon application of a biasing force, is elongatable, at least about 70%, more preferably at least about 100%, and even more preferably about 120% without offering a significant resistance force (less than 10 g/cm) or experiencing catastrophic failure.

As used herein, the terms "melt-stabilized" or "weakened" refers to portions of a web which have been subjected to localized heating and/or localized pressure to substantially consolidate the fibers of the web into a stabilized film-like form.

As used herein, the term "machine direction" is used herein to refer to the primary direction of material or web flow through a process or line.

As used herein, the term "cross machine direction" or "cross machine directional" is used herein to refer to a direction that is generally perpendicular to, or perpendicular to, the machine direction.

The present disclosure is directed generally to methods of making zoned apertured webs or zoned apertured nonwoven webs. In general, a web or nonwoven web with primary bonds is provided. The primary bond patterns may be those currently commercially supplied by Fitessa or Pegas Nonwovens, for example. The primary bonds generally function to hold fibers, such as nonwoven fibers, together and enable the web to maintain its structure once the fibers are laid down.

The webs are first unrolled and advanced in a machine direction. The webs may then be weakened at a plurality of first locations in a first zone and at a plurality of second locations in a second zone (see e.g., FIG. 1 for the weakened locations in the two zones). The first and second zones may alternate along the web in the machine direction as the web is advanced in the machine direction. In other instances, more than two zones may alternate along the webs in the machine direction (e.g., zone 1, zone 2, zone 3, zone 1, zone 2, zone 3 etc.). The first plurality of weakened locations in the first zone may have a different pattern and/or orientation as the second plurality of weakened locations in the second zone. Furthermore, each of, or some of, the weakened locations in the first zone may be smaller or larger (e.g., CD width and/or MD length) than the weakened locations in the second zone. Similarly, each of, or some of, the weakened locations in the first zone may have a different shape than each of, or some of, the weakened locations in the second zone. An overbonding step may be used to form the weakened locations, as will be discussed further herein. The overbonding step may comprise applying heat and/or pressure to the web using an overbonding roll and an anvil or other suitable processes known to those of skill in the art.

Once the first and second pluralities of weakened locations are formed in the various zones of the web, the web may continue to be advanced in the machine direction to an incrementally stretching apparatus. The incrementally stretching apparatus may locally extend portions of the web in a direction substantially parallel to, or parallel to, a cross machine direction to cause the web to at least partially, or fully, rupture at all of, most of, or some of the first and second pluralities of weakened locations in the first and second zones, respectively, to begin formation of apertures, or fully create apertures, at all of, most of, or some of the weakened locations. Next, the web may be subjected to a cross machine directional tensioning apparatus to cause the web to further define or further form all of, most of, or some of the first and second pluralities of weakened locations into apertures or at least partially into apertures. The cross machine directional tensioning force applied by the cross machine directional tensioning apparatus may be in the range of about 8 grams to about 25 grams, about 10 grams to about 20 grams, about 13 grams to about 17 grams, or about 15 grams, specifically reciting all 0.1 gram increments within the specified ranges and all ranges formed therein or thereby. The cross machine directional tensioning force may be constant, or substantially constant, in the various zones of the web. Further, the cross machine directional tensioning force may be reduced or increased depending on the properties (e.g., basis weight, extensibility) of the web being formed. This further definition of the apertures caused by the cross machine directional tensioning force may form a plurality of first apertures in the web coincident with all of, most of, or some of the first plurality of weakened locations in the first zone and a plurality of second apertures in the web coincident with all of, most of, or some of the second plurality of weakened locations in the second zone (see e.g., FIG. 2 for a web having different apertures in two zones). The first plurality of apertures in the first zone may all have about the same effective aperture areas and/or the same shapes or may have different effective aperture areas and/or different shapes. The plurality of second apertures in the second zone may all have about the same effective aperture areas and/or the same shapes or may have different effective apertures areas and/or different shapes. In some instances, the plurality of first apertures in the first zone may have different effective aperture areas, sizes, different patterns, and/or different shapes as the plurality of second apertures in the second zone. Furthermore, the plurality of first apertures in the first zone may have the same effective aperture area and/or same shape as the plurality of second apertures in the second zone, but may be arranged in a different pattern as the plurality of second apertures in the second zone.

In one form, the plurality of apertures in the first zone may have an effective aperture area, according to the Aperture Test herein, in the range of about 0.1 mm² to about 6 mm², about 0.3 mm² to about 5 mm², about 0.5 mm² to about 4 mm², about 0.7 mm² to about 3.5 mm², about 0.8 mm² to about 3 mm², or about 0.8 mm² to about 2.96 mm², specifically reciting all 0.1 mm² increments within the above-specified ranges and all ranges formed therein or thereby.

In one form, the plurality of apertures in the second zone may have an effective aperture area, according to the Aperture Test herein, in the range of about 1 mm² to about 12 mm², about 2 mm² to about 10 mm², about 3 mm² to about 8 mm², about 4 mm² to about 8 mm², about 5 mm² to about 7 mm², about 5.17 mm² to about 5.66 mm², about 5 mm², about 5.2 mm², about 5.5 mm², about 5.6 mm², or about 5.7 mm², specifically reciting all 0.1 mm² increments within the above-specified ranges and all ranges formed therein or thereby.

The weakening step (e.g., overbonding) described above may be performed at an absorbent article making facility either as part of the absorbent article forming line or as a separate operation. Alternatively, the webs may be provided to, for example, absorbent article manufacturers, with the weakened locations already within the web. Although absorbent article manufactures are used as examples herein, the webs of the present disclosure may be incorporated into any suitable products made by any type of manufactures. The incrementally stretching step and/or cross machine directional tension step may also be performed at the manufacturer of the final product incorporating the webs or at the web manufacturer.

Figure 2:
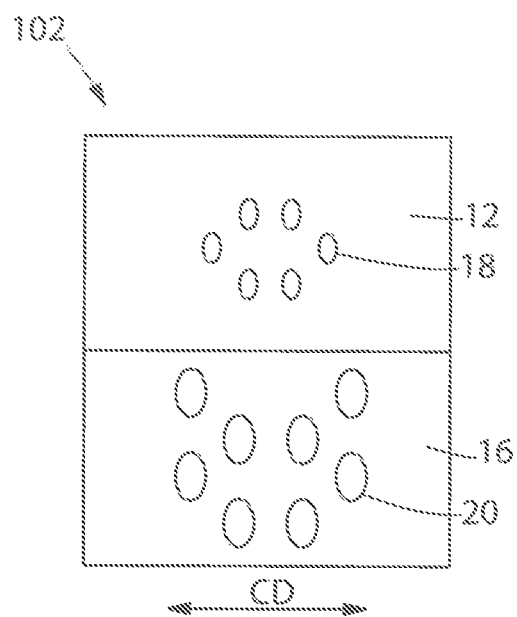
FIG. 2 is a schematic representation of the example web of FIG. 1 after localized incremental stretching (cross machine direction) and after applying a cross machine directional tensioning force to the web to create a first plurality of apertures in the first zone and a second plurality of apertures in the second zone in accordance with the present disclosure.

A schematic example of a web 102, after being cut into discrete portions, having a first plurality of weakened locations 10 in a first zone 12 and a second plurality of weakened locations 14 in a second zone 16 is illustrated in FIG. 1. The first plurality of weakened locations are illustrated as having a different pattern and a different size as the second plurality of weakened locations. FIG. 2 illustrates the web 102 after each of the first and second plurality of weakened locations 10 and 14 have been ruptured by localized incremental stretching and by application of a cross machine directional tensioning force to create a plurality of first apertures 18 in the first zone 12 and a plurality of second apertures in 20 in the second zone 16. As one example, the web 102 with the plurality of different apertures in different zones may be used as a topsheet in an absorbent article, with the first zone 12 at least partially forming a front region of the absorbent article and the second zone 16 at least partially forming the back region of the absorbent article. The first zone 12 may be configured to receive urine and the second zone 16 may be configured to receive bowel movements, or running bowel movements. As such, typically, the effective aperture area of the apertures in the second zone 16 may be larger than the effective aperture area in the first zone 12. The web growth in the cross machine direction (CD arrow) in the web 102 between FIGS. 1 and 2 should be noted. This cross machine directional web growth is due to the localized incremental stretching of the web and the cross machine directional tensioning force. The web growth in both the first and second zones 12 and 16 may be in the range of about 2 mm to about 10 mm, about 3 mm to about 8 mm, about 4 mm to about 7 mm, about 5 mm, about 5.5 mm, or about 6 mm, specifically reciting all 0.1 mm increments within the specified ranges and all ranged formed therein or thereby. The web growth in the first zone 12 and the second zone 16 may be constant, or substantially constant (i.e., within +/−3 mm, within +/−2 mm or less, or within +/−1 mm or less). Typically, when two different patterns, areas, sizes, and/or orientations of apertures are formed in two different zones of a web, the cross machine directional width is not substantially constant in the two different zones (e.g., it is greater than a 3 mm or greater than a 4 mm difference in the cross machine directional width in the first and second zones), owing to the fact that one zone stretches more in the cross machine direction than the other zone because of the different aperture areas, sizes, patterns, and/or orientations. In the methods of the present disclosure, it has been discovered how to maintain constant, or substantially constant, cross machine directional widths in different zones, each having different patterns, areas, sizes, and/or orientations of apertures.

Figure 3:
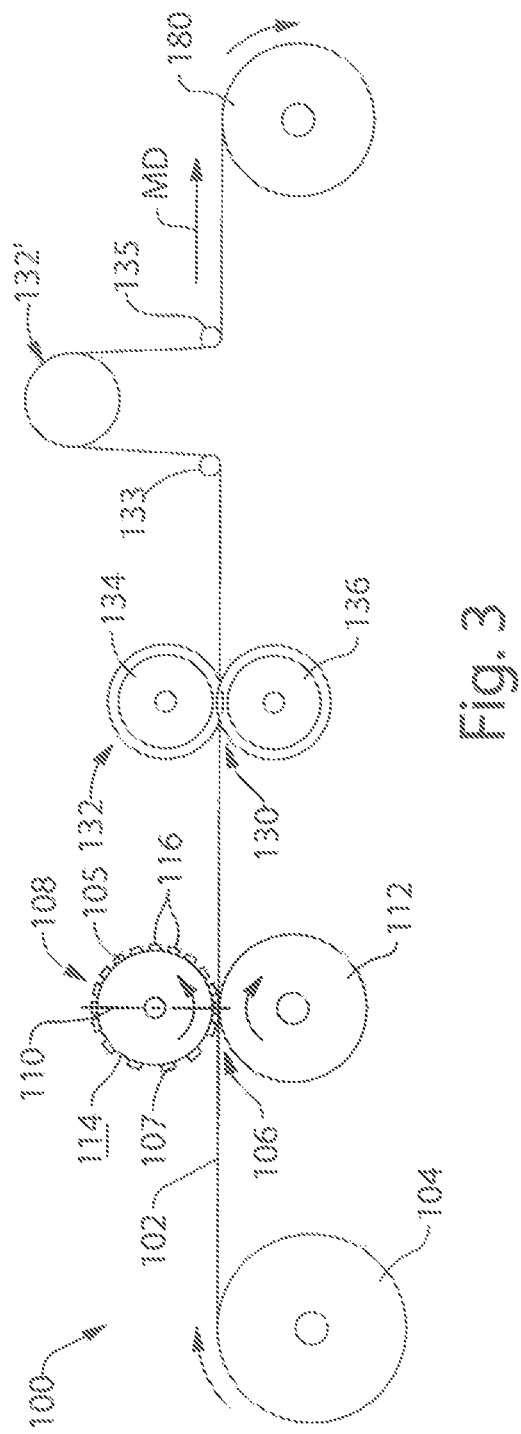
FIG. 3 is a schematic representation of an example method for making a zoned apertured web in accordance with the present disclosure.

Now referring to FIG. 3, there is schematically illustrated at 100 a process for making a zoned apertured web that, for example, may be suitable for making a topsheet for an absorbent article. A precursor web or precursor nonwoven web 102 (without weakened locations) may be supplied as the starting material from a web supplier. The precursor web 102 may comprise primary bonds added by the web manufacturer during web formation to maintain the integrity of the web 102 and hold the nonwoven fibers together. The precursor nonwoven web 102 may be supplied as discrete webs (e.g., sheets or patches) of material for batching processing. For commercial processing, however, the precursor nonwoven web 102 may generally be supplied as roll stock, and, as such it can be considered as having a finite width and an infinite length. In this context, the length of the web 102 is measured in the machine direction and the width is measured in the cross machine direction. The web 102 may be extensible, elastic, or nonelastic, as long as it can be processed by the methods described herein and retain the properties described herein. The web 102 may also be formed of one or more layers of fibers, such as meltblown fibers, spunbond fibers, microfibers, nanofibers, bicomponent fibers, and/or carded fibers, for example. The webs 102 may have a basis weight in the range of about 15 gsm to about 60 gsm, about 20 gsm to about 40 gsm, about 20 gsm to about 30 gsm, about 22 gsm to about 30 gsm, about 25 gsm, about 26 gsm, about 27 gsm, about 28 gsm, or about 29 gsm, specifically including all 0.1 gsm increments within the specified ranges and all ranges formed therein or thereby, although other basis weights may be appropriate for various applications. Bicomponent nonwoven materials may be used, such as an about 28 gsm bicomponent nonwoven material, for example. The precursor nonwoven web 102 may also be joined to one or more polymeric films, one or more carded materials, one or more nonwoven materials, and/or one or more other materials to form a laminate.

Still referring to FIG. 3, the precursor web 102 may be unwound from a supply roll 104 and may travel in a direction indicated by the MD arrow as the supply roll 104 rotates in the direction indicated by the arrow associated therewith. The precursor web 102 may also be supplied to the line using any other suitable web supply equipment. The nonwoven web 102 may then be advanced in the machine direction and pass through a nip 106 of the web weakening apparatus 108 formed by rolls 110 and 112. The roll 110 may be an overbonding roll and the roll 112 may be an anvil, such as a smooth steel or rubber anvil roll. The rolls 110 and 112 may have a Rockwell Hardness in the range of about 55 to about 65 or in the range of about 58 to about 62, specifically including all 0.1 Rockwell Hardness value increments within the specified ranges or any ranges formed therein or thereby, or any other suitable Rockwell Hardness values depending on the material being passed through the rolls 110 and 112. The overbonding roll 110 and anvil roll 112 may be used to perform localized web weakening in the form of an overbonding step. The force between the rolls 110 and 112 may be about 110 psi to about 200 psi, specifically including all 0.1 psi increments with the specified ranges and all ranges formed therein. The overbonding roll and the anvil roll may be reversed in position while still achieving the same result. Optionally, the overbonding roll and/or the anvil roll may be heated to a temperature in the range of about 130 degrees Celsius to about 180 degrees Celsius, specifically reciting all 0.1 degree Celsius increments within the specified ranges and all ranged formed therein, to aid in weakening of the plurality of locations in the web 102. In other instances, neither, or only one, roll may be heated. The pressure between the two rolls may be adjusted by well known methods to provide the desired temperature, if any, and pressure to concurrently weaken and melt-stabilize the nonwoven web 102 at the plurality of first and second locations 10 and 14, respectively.

Figure 4:
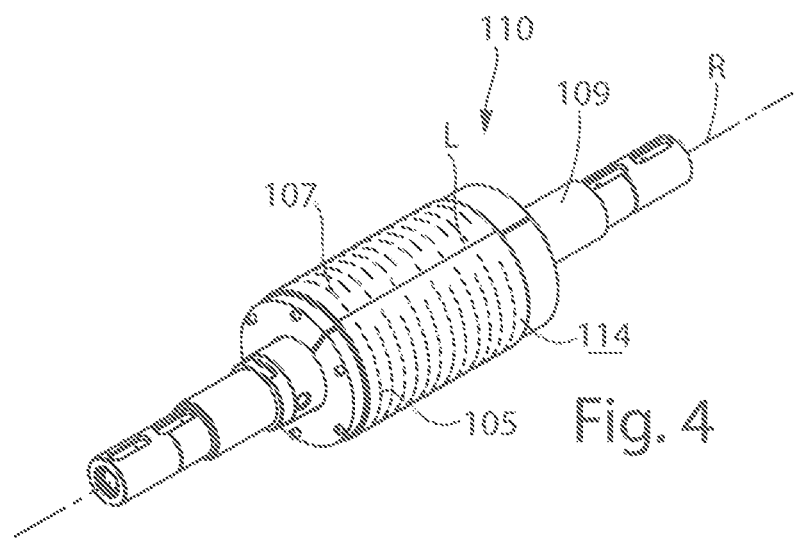
FIG. 4 is a perspective view of an example overbonding roll used in the methods for making a zoned apertured web in accordance with the present disclosure.

Referring to FIG. 4, a perspective view of an example overbonding roll 110 for use as roll 110 of the web weakening apparatus 108 of the present disclosure is illustrated. The example overbonding roll 110 may comprise a first pattern of radially outwardly extending protrusions 105 on a first portion of a radial outer surface 114 of the overbonding roll 110 and a second pattern of radially outwardly extending protrusions 107 positioned on a second portion of the radial outer surface 114 of the overbonding roll 110. The first pattern of radially outwardly extending protrusions 105 may extend around about 50%, or 50%, of the circumference of the overbonding roll 110 in the direction of rotation of the overbonding roll, with the second pattern of radially outwardly extension protrusions 107 completing the circumference of the overbonding roll. Typically, an imaginary line, L, generally parallel with the rotational axis, R, of the roll will be formed at the intersection of the first pattern of protrusions 105 and the second pattern of protrusions 107. The overbonding roll 110 may be mounted on a rotating shaft 109. In other forms, the overbonding roll 110 may rotate relative to the rotating shaft 109 via bearings and may be driven by the anvil roll 112 or by other drive mechanisms known to those of skill in the art. As an example, the overbonding roll may have a circumference in the range of about 17 inches to about 40 inches, a diameter in the range of about 5 inches to about 12 inches and a cross machine directional width in the range of about 1.57 inches to about 11.81 inches, specifically including all 0.1 inch increments with the specified ranges and all ranges formed therein. Other suitable dimensions of the overbonding roll are also within the scope of the present disclosure depending on the particular material being manufactured.

While the overbonding roll can have any suitable dimensions for a particular application, the circumferential length of the first zone and/or first pattern of protrusions (if throughout the first zone), in the direction of rotation of the roll, may correspond with the desired machine directional length in the web where the first zone and/or the first plurality of weakened locations are desired. An as example, if the first zone and/or the first pattern of protrusions (if throughout the first zone) on the overbonding roll has a circumferential length in the direction of rotation of the roll of 10 inches, the first zone in the web 102 will be about 10 inches. The same applies to the second pattern. It is to be noted that the first zone and the second zone of the roll 110 may or may not have protrusions throughout their entire area in the machine direction or the cross machine direction depending on the desired patterns of weakened locations in the web.

In some instances, it may be desirable to have the first zone and/or the first pattern of protrusions or the second zone and/or the second pattern of protrusions extend circumferentially around the roll in different circumferential lengths. For example, the first zone and/or the first pattern of protrusions may extend around 60% of the circumferential length of the roll and the second zone and/or the second pattern of protrusions may only extend around 40% of the circumferential length of the roll. Those of skill in the art will recognize many other variations of the circumferential lengths of the two zones and/or patterns (e.g., first zone/pattern 90%, second zone/pattern 10%; first zone/pattern 30%, second zone/pattern 70%; first zone/pattern 30%, second zone/pattern 50%, 20% no pattern etc.). This may be desirable for some applications if it is helpful that the first zone's machine direction length on the web be shorter or longer than the second zone's machine direction length on the web 102 or if a gap is desired between the two zones of weakened locations.

In other situations, it may be desirable to provide more than two patterns of protrusions and/or more than two zones on a particular overbonding roll, such that the weakened web has three or more different zones and/or patterns of weakened locations. All of the weakened locations in the three or more zones may be the same or different in area, size, pattern, and/or orientation. In still other instances, it may be desirable to make the diameter of the roll larger and alternate between the first and second patterns, or more than two patterns, about the circumference of the roll. In such an instance, the roll may overbond using the first pattern, then the second pattern, then the first pattern (but at a different location on the roll), then the second pattern (but at a different location on the roll), then back to the original first pattern. Gaps may be formed between one or more of the various patterns, if desired. These four patterns of protrusions may have an equal circumferential length (e.g., 25%, 25%, 25%, and 25%) or different circumferential lengths (e.g., 20%, 30%, 20%, and 30%; or 15%, 35%, 15%, and 35%). Gaps may also be provided between the various patterns of protrusions, if desired. Those of skill in the art will recognize the multiple variations of the patterns of the protrusions and/or zones on the overbonding roll. The patterns of protrusions and/or zones may not only vary about the circumference of the overbonding roll, but may also vary along a direction parallel to the rotational axis, R, of the overbonding roll (see FIG. 4). As stated above, some areas of the overbonding roll may not comprise any protrusions because certain areas of the produced web do not require weakened locations that are formed into apertures.

Figure 5:
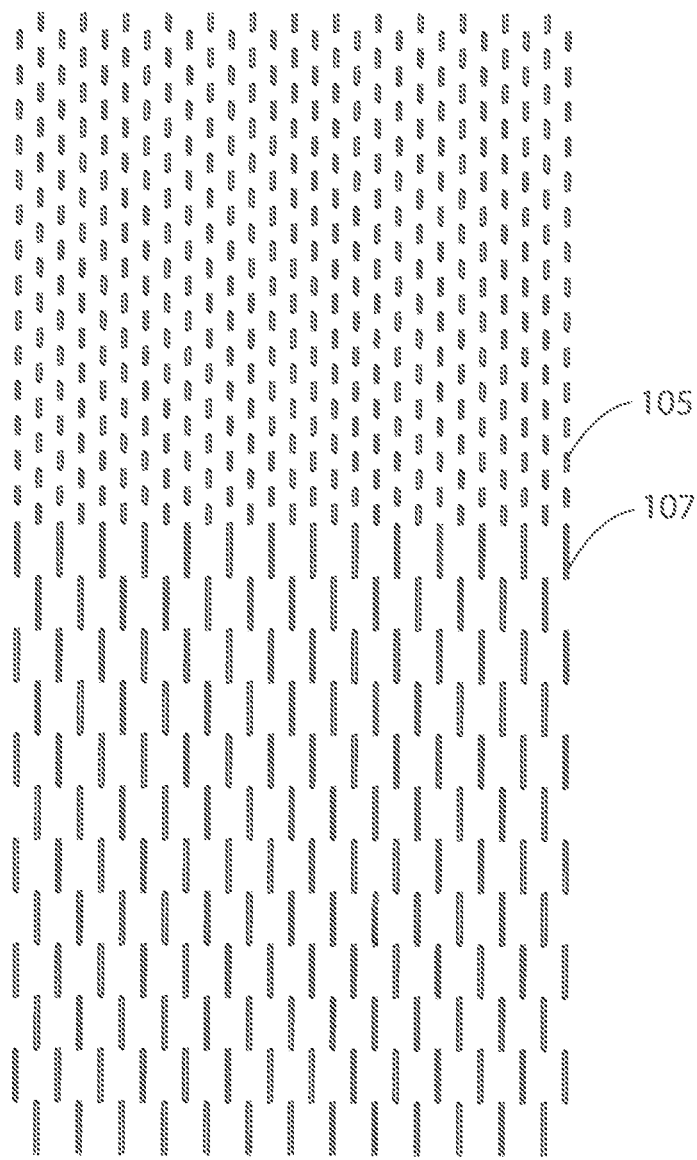
FIG. 5 is an example of a portion of a radial outer surface of an overbonding roll having two different patterns of protrusions in two different zones in accordance with the present disclosure.
Figure 6:
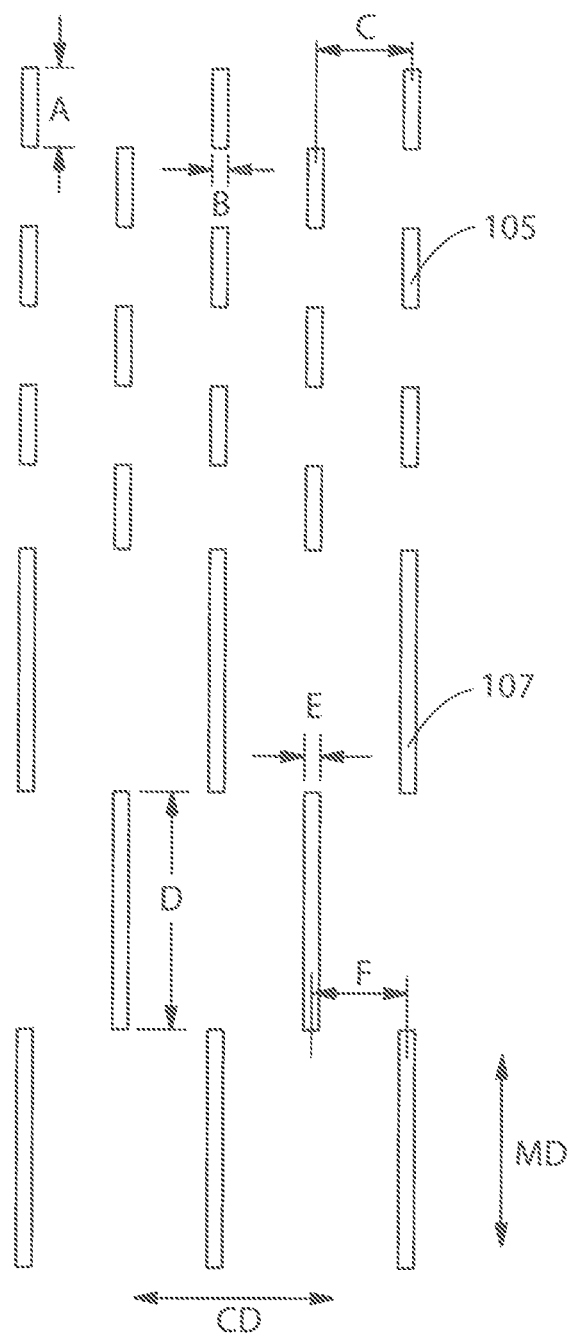
FIG. 6 is a schematic representation of two different patterns of protrusions in two different zones on a radial outer surface of an overbonding roll in accordance with an example of the present disclosure.
Figure 7:
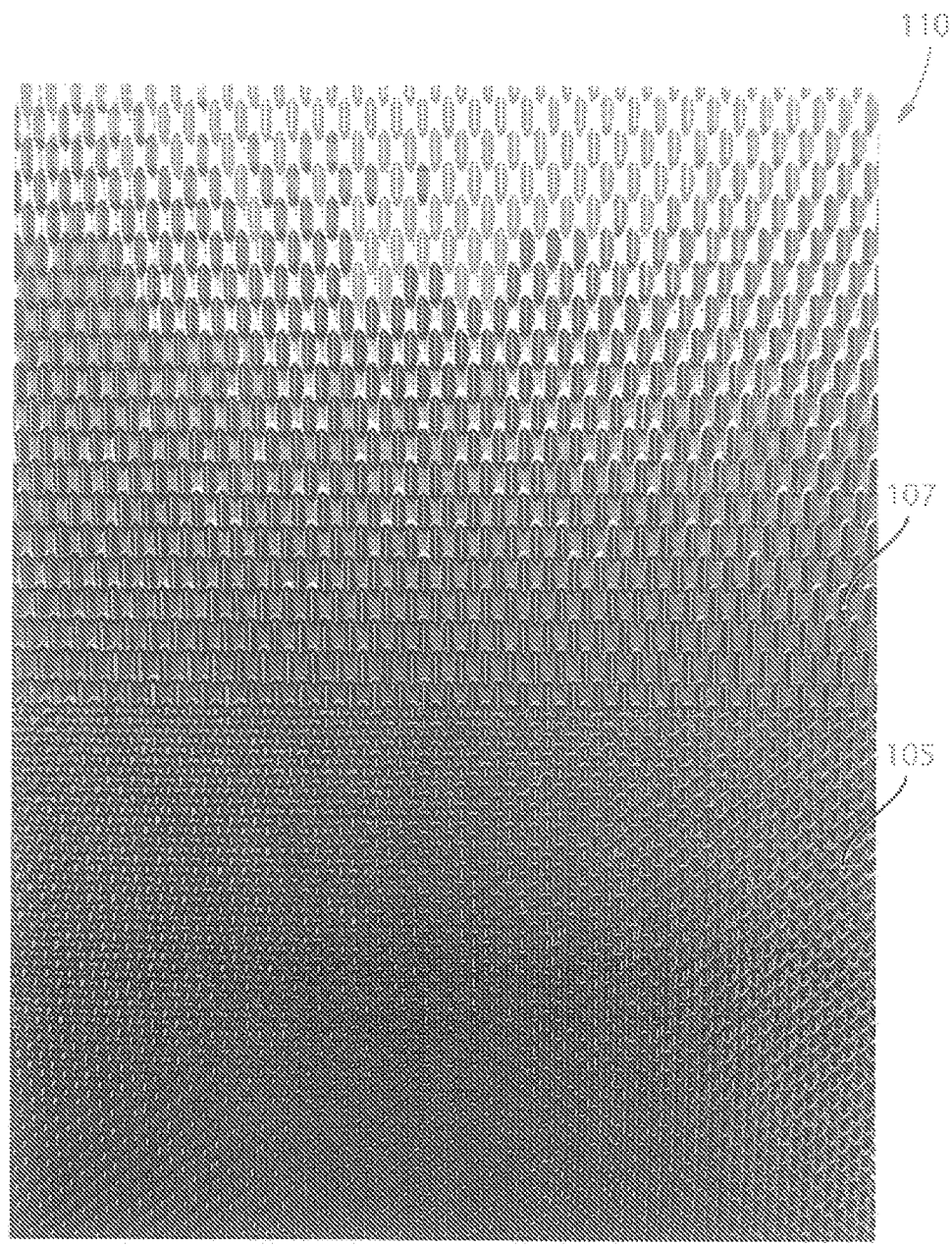
FIG. 7 is a photograph of two portions of a radial outer surface of an overbonding roll having different patterns of protrusions in accordance with an example of the present disclosure.

Some example first and second patterns of the protrusions 105 and 107, respectively, for the overbonding roll 110 are shown in FIG. 5. FIG. 6 is a drawing of the first and second patterns of the protrusions 105 and 107, respectively, on a portion of the overbonding roll 110. FIG. 7 is a photograph of the first and second patterns of the protrusions 105 and 107, respectively, on a portion of an example overbonding roll 110.

Referring again to FIG. 6, in one form, the first plurality of protrusions 105 on the overbonding roll 110 may be about 1.27 mm long (MD direction—distance "A") and about 0.25 mm wide (CD direction—distance "B") and have a cross machine directional spacing of about 1.52 mm (center to center—distance "C"). There may or may not be any machine direction overlap of the first plurality of protrusions. In one form, the second plurality of protrusions 107 on the overbonding roll 110 may be about 3.81 mm long (distance "D") and about 0.25 mm wide (distance "E") and have a cross machine directional spacing of about 1.52 mm (center to center-distance "F"). There may or may not be any machine direction overlap of the second plurality of protrusions 107. Alternatively, in another form, the first plurality of protrusions 105 on the overbonding roll 110 may be about 1.20 mm to about 1.30 mm long (distance "A") and about 0.2 mm to about 0.3 mm wide (distance "B") and have a cross machine directional spacing of about 1.50 mm to about 1.60 mm (center to center-distance "C"). There may or may not be any machine direction overlap of the first plurality of protrusions 105. In another form, the second plurality of protrusions 107 on the overbonding roll 110 may be about 3.80 mm to about 3.90 mm long (distance "D") and about 0.2 mm to about 0.3 mm wide (distance "E") and have a cross machine directional spacing of about 1.50 mm to about 1.60 mm (center to center-distance "F"). There may not be any machine direction overlap of the second plurality of protrusions 107. Again, alternatively, in another form, the first plurality of protrusions 105 on the overbonding roll 110 may be about 1.0 mm to about 1.60 mm long (distance "A") and about 0.1 mm to about 0.4 mm wide (distance "B") and have a cross machine directional spacing of about 1.30 mm to about 1.90 mm (center to center-distance "C"). There may or may not be any machine direction overlap of the first plurality of protrusions 105. In another form, the second plurality of protrusions 107 on the overbonding roll 110 may be about 3.20 mm to about 4.5 mm long (distance "D") and about 0.1 mm to about 0.4 mm wide (distance "E") and have a cross machine directional spacing of about 1.30 mm to about 1.90 mm (center to center-distance "F"). There may or may not be any machine direction overlap of the second plurality of protrusions 107. The first plurality of protrusion may all have the same dimensions and/or spacing relative to each other, or may have different dimensions and/or spacing relative to each other. The same applies to the second plurality of protrusions. In one form, the first plurality of protrusions may be configured to form smaller or larger weakened locations in a web than the second plurality of protrusions.

Figure 8:
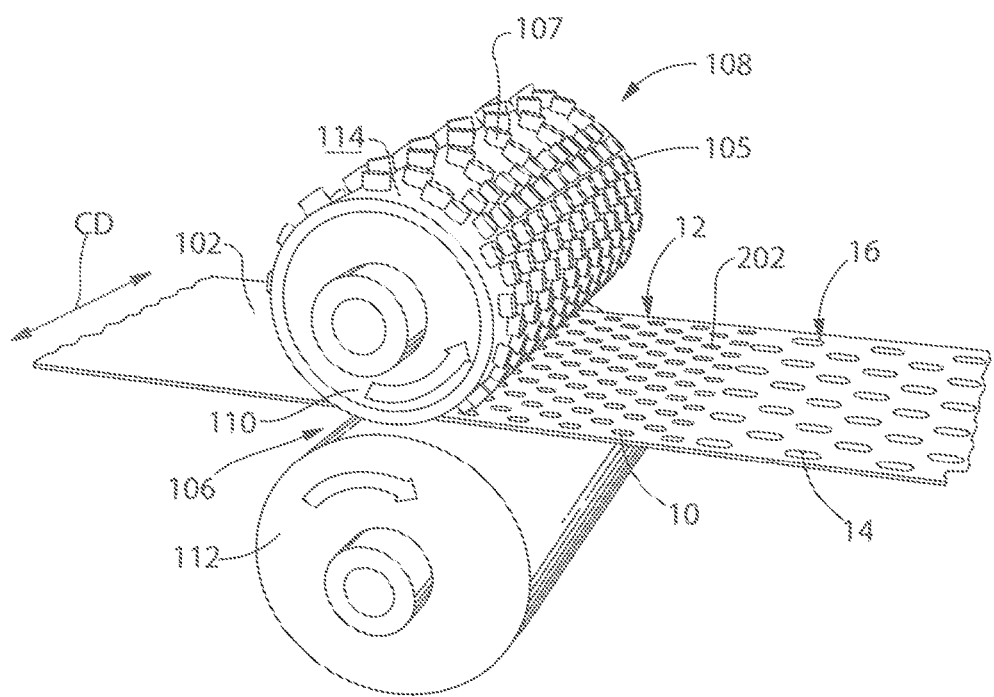
FIG. 8 is a perspective illustration of an example web weakening apparatus in accordance of the present disclosure.

Referring to FIG. 8, a perspective view of an example web weakening apparatus 108 is illustrated. The weakening apparatus 108 may comprise the overbonding roll 110 and the anvil roll 112. The web 102 is passed through the nip 106 formed between the overbonding roll 110 and the anvil roll 112. The first and second patterns of protrusions 105 and 107 on the overbonding roll 110 form alternating machine direction first and second zones 12 and 16 in the web 102, wherein the first zone 12 has the first plurality of weakened locations 10 and the second zone 16 has the second plurality of weakened locations 14. The weakened locations 14 in the second zone 16 may generally be larger or have a greater area than the weakened locations 10 in the first zone 12 or vice versa. Furthermore, the weakened locations 10 in the first zone 12 may have a different pattern and/or orientation as the weakened locations 14 in the second zone 16. The rolls 110 and 112 may rotate in the directions shown by the arrows.

Referring again to FIG. 3, owing to a localized incremental stretching apparatus 132, the nonwoven web 102 may be stretched in the cross machine direction through a tensioning force to rupture at least some of, most of, or all of the first and second plurality of weakened, melt-stabilized locations 10 and 14 in the web 102, thereby at least partially creating or rupturing a first and second plurality of apertures 18 and 20 in the nonwoven web coincident with the first and second pluralities of weakened, melt-stabilized locations 10 and 14. The web 102 may be passed through a nip 130 formed by a first incremental stretching roll 134 and a second incremental stretching roll 136. Both of the rolls 134 and 136 may have three-dimensional surfaces which at least to a degree are complementary to one another and intermesh with each other.

Figure 9:
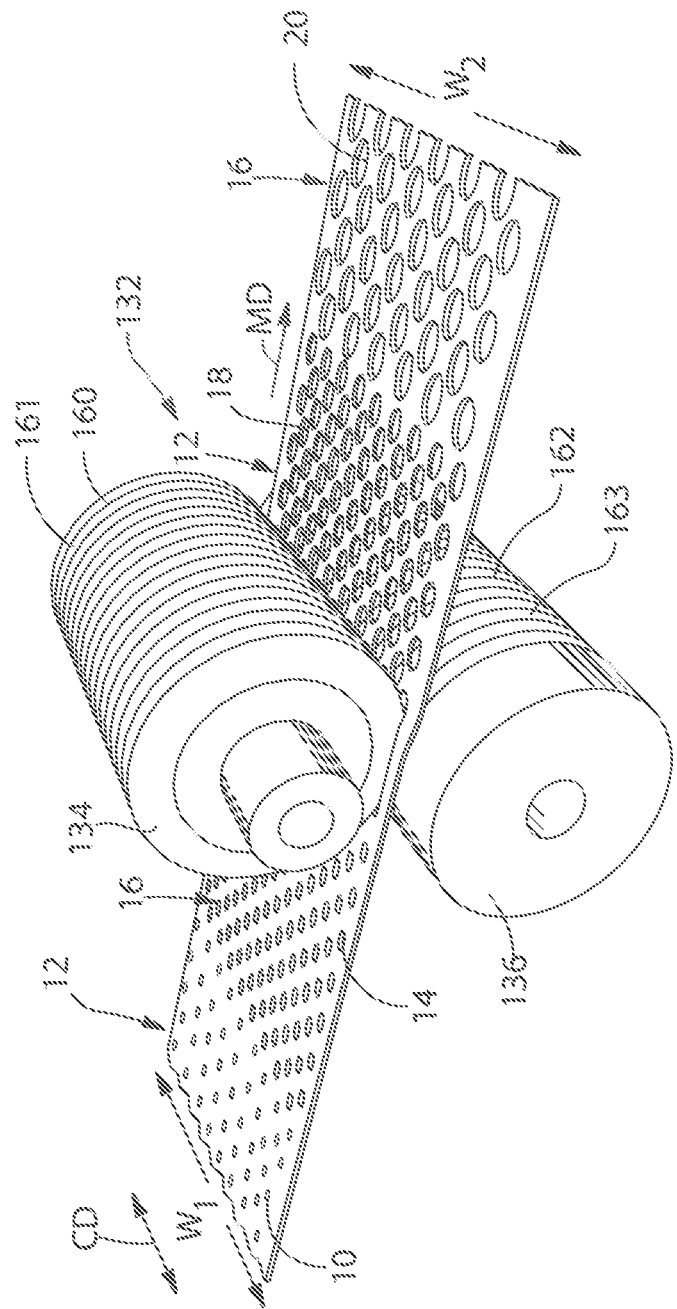
FIG. 9 is perspective view of an example apparatus for incrementally stretching a zoned web in accordance with the present disclosure.
Figure 10:
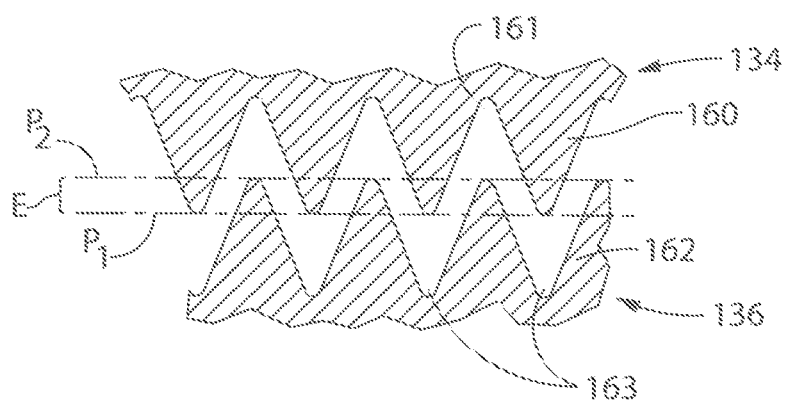
FIG. 10 is an enlarged illustration showing the details of teeth of the incremental stretching apparatus of FIG. 9 in accordance with the present disclosure.

Referring to FIGS. 9 and 10, there is shown a perspective view of the incremental web stretching apparatus 132 comprising incremental stretching rolls 134 and 136. The incremental stretching roll 134 includes a plurality of teeth 160 and corresponding grooves 161 which extend about the entire circumference of roll 134, or in some instances, extend less than the entire circumference of the roll. The incremental stretching roll 136 includes a plurality of teeth 162 and a plurality of corresponding grooves 163. The teeth 160 on the roll 134 intermesh with or engage the grooves 163 on the roll 136, while the teeth 162 on the roll 136 intermesh with or engage the grooves 161 on the roll 134. The teeth on each roll may be generally triangular-shaped, as shown in FIG. 10, or otherwise suitably shaped. The apex of the teeth may be slightly rounded, if desired for certain features in the finished web. As can be seen in FIG. 9, the first and second pluralities of weakened locations 10 and 14 are at least partially formed into first and second pluralities of apertures 18 and 20, respectively, by the incremental web stretching apparatus 132.

With reference again to FIG. 10, which shows a portion of the intermeshing of the teeth 160 and 162 of the rolls 134 and 136, respectively, the term "pitch" refers to the distance between the apexes of adjacent teeth. The pitch may be between about 0.02 inches to about 0.30 inches (about 0.51 mm to about 7.62 mm) or may be between about 0.05 inches and about 0.15 inches (about 1.27 mm to about 3.81 mm) The height (or depth) of the teeth is measured from the base of the tooth to the apex of the tooth, and may or may not be equal for all teeth. The height of the teeth may be between about 0.10 inches (about 2.54 mm) and about 0.90 inches (about 22.9 mm) or may be between about 0.25 inches (about 6.35 mm) and about 0.50 inches (about 12.7 mm).

The teeth 160 in one roll can be offset by about one-half of the pitch from the teeth 162 in the other roll, such that the teeth of one roll (e.g., teeth 160) mesh in the valley (e.g., valley 163) between teeth in the mating roll. The offset permits intermeshing of the two rolls when the rolls are "engaged" or in an intermeshing, operative position relative to one another. The teeth of the respective rolls may only be partially intermeshing. The degree to which the teeth on the opposing rolls intermesh is referred to herein as the "depth of engagement" or "DOE" of the teeth. The DOE may be constant or not constant. As shown in FIG. 10, the DOE, E, is the distance between a position designated by plane P1 where the apexes of the teeth on the respective rolls are in the same plane (0% engagement) to a position designated by plane P2 where the apexes of the teeth of one roll extend inward beyond the plane P1 toward the valley on the opposing roll. The optimum or effective DOE for particular laminate webs is dependent upon the height and the pitch of the teeth and the materials of the web. It is important to note that the web 102 having the different (e.g., different patterns, effective aperture areas, sizes, and/or orientations) first and second weakened locations 10 and 14 can experience constant, or substantially constant, web growth in the cross machine direction with the constant DOE. Some example DOEs may in the range of about 0.01 inches to about 0.5 inches, about 0.03 inches to about 0.2 inches, about 0.04 inches to about 0.08 inches, about 0.05 inches, or about 0.06 inches, specifically reciting all 0.001 inch increments within the above-specified ranges and all ranges formed therein or thereby.

In some situations, the teeth of the mating rolls need not be aligned with the valleys of the opposing rolls. That is, the teeth may be out of phase with the valleys to some degree, ranging from slightly offset to greatly offset.

As the nonwoven web 102 having first and second weakened, melt-stabilized locations 10 and 14 passes through the incremental web stretching apparatus 132 the nonwoven web 102 is subjected to tensioning in the cross machine direction, or substantially in the cross machine direction, thereby causing the nonwoven web 102 to be extended in the cross machine direction. The tensioning force placed on the nonwoven web 102 may be adjusted by varying the pitch, DOE, or teeth size, such that the incremental stretching is sufficient to cause the first and second weakened, melt-stabilized locations 10 and 14 to at least partially, or fully, rupture, thereby creating, or at least partially creating, a first and second plurality of apertures 18 and 20 coincident with the first and second weakened, melt-stabilized locations 10 and 14 in the nonwoven web 102. However, at least most of, or all of, the primary bonds of the precursor nonwoven web 102 typically do not rupture during tensioning, thereby maintaining the nonwoven web in a coherent condition even as the first and second weakened, melt-stabilized locations 10 and 14 rupture, or at least partially rupture. The cross machine directional tensioning force applied by the incremental web stretching apparatus 132 may be in the range of about 8 grams to about 30 grams or about 12 grams to 18 about grams, specifically reciting all 0.1 gram increments within the specified ranges and all ranges formed therein or thereby. Other cross machine directional tensioning forces may also be used depending on the materials and properties of the web being produced.

Referring again to FIG. 9, after passing through the incremental web stretching apparatus 132, the nonwoven web 102 may have a cross machine directional width, W2, that is greater than the width, W1, of the precursor web 102, first and second at least partially formed apertures 18 and 20, respectively, in the first and second zones 12 and 18, respectively, where the first and second weakened, melt-stabilized regions 10 and 14 ruptured or at least partially ruptured, and increased extensibility in the cross machine direction. The actual width, W2, in the cross machine direction is somewhat dependant on the amount of machine direction tension applied to the web 102 when it exits the incremental web stretching apparatus 132. As expected, narrowing, and even necking of the web 102 may be achieved by increasing the tension in the machine direction sufficiently.

Some machine direction tensions that are suitable for the methods of the present disclosure are in the range of about 8 grams to about 30 grams, about 10 grams to about 20 grams, or about 12 grams to about 18 grams, specifically reciting all 0.1 gram increments within the above-specified ranges and all ranges formed therein or thereby.

Other example structures of incremental stretching apparatuses suitable for incrementally stretching or tensioning of a web are described in U.S. Pat. No. 5,518,801, issued to Chappell et al., on May 21, 1996.

Figure 11A:
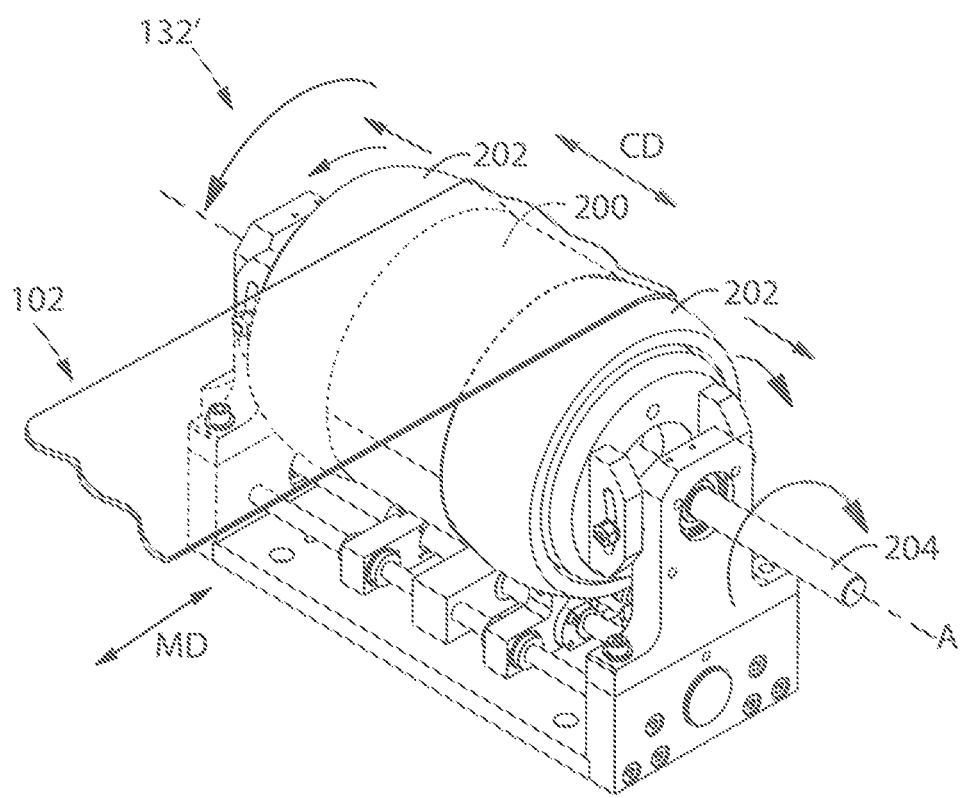
FIG. 11A is a top perspective view of an example cross machine directional tensioning apparatus in accordance with the present disclosure.

After the web 102 passes through the incremental web stretching apparatus 132, the web 102 may be advanced to and at least partially around a cross machine directional tensioning apparatus 132' (see e.g., FIGS. 3 and 11A). The cross machine directional tensioning apparatus 132' may be offset from the main processing line by running the web partially around two idlers 133 and 135 or stationary bars, for example. In other instances, the cross machine tensioning apparatus 132' may be positioned in line with the main processing line. The cross machine directional tensioning apparatus 132' may comprise a roll that comprises at least one outer longitudinal portion that expands along a longitudinal axis, A, of the roll, relative to a middle portion of the roll, to stretch and/or expand the web 102 in the cross machine direction. Instead of or in addition to expanding along the longitudinal axis, A, of the roll, the outer longitudinal portion may be angled relative to the longitudinal axis, A, of the roll in a direction away from the web 102 being advanced over the roll to stretch the web 102 in the cross machine direction or substantially in the cross machine direction. Optionally, the roll may comprise two outer longitudinal portions that each expand in opposite directions generally along the longitudinal axis, A, of the roll. The two outer portions may both be angled downwards in a direction away from the web 102 being advanced over the roll. This movement or positioning of the outer longitudinal portions of the roll allows for generally cross machine directional tensioning of the web 102 which causes the plurality of first and second weakened regions 10 and 12 to rupture and/or be further defined or formed into the first and second apertures 18 and 20, respectively. The outer longitudinal portions of the roll may comprise vacuum, a low tack adhesive, a high coefficient of friction material or surface, such as rubber, and/or other mechanisms and/or materials to hold the web 102 to the outer lateral portions of the roll during movement of the outer longitudinal portion or portions relative to the middle portion of the roll. The vacuum, low tack adhesive, high coefficient of friction material or surface, and/or other mechanisms and/or materials may prevent, or at least inhibit, the held portions of the web from slipping relative to the longitudinal axis, A, of the roll during stretching of the outer lateral portions of the web in the cross machine direction or generally in the cross machine direction.

FIG. 11A is a top perspective view of the example cross machine directional tensioning apparatus 132'. The cross machine directional tensioning apparatus 132' may comprise a roll comprising a middle portion 200 and two outer longitudinal portions 202 situated on either end of the middle portion 200. The roll may rotate about its longitudinal axis, A, on a drive shaft 204. The roll may rotate relative to the drive shaft 204 or in unison with the drive shaft 204, as will be recognized by those of skill in the art. The web 102 may be advanced over the entire cross machine directional width of the middle portion 200 and at least portions of the cross machine directional widths of the outer longitudinal portions 202. The web 102 may be advanced over at least about 5% up to about 80% of the circumference of the roll so that the cross machine directional stretching may be performed.

Figure 11B:
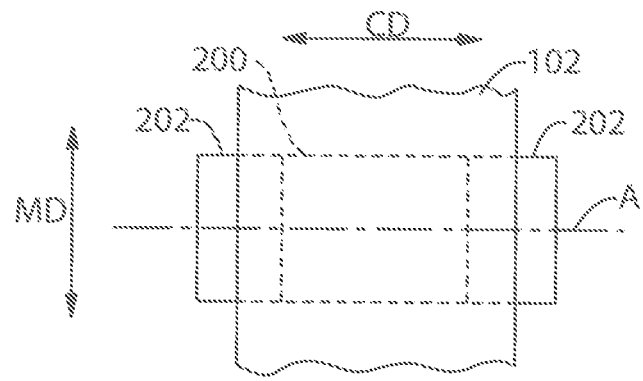
FIG. 11B is a schematic representation of a front view of an example cross machine directional tensioning apparatus with outer longitudinal portions in an unexpanded and non-angled position relative to a middle portion in accordance with the present disclosure.
Figure 11C:
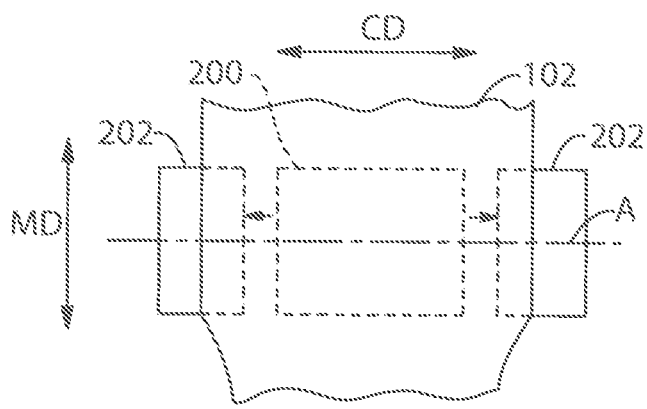
FIG. 11C is a schematic representation of a front view of the cross machine directional tensioning apparatus of FIG. 11B with the outer longitudinal portions in a longitudinally expanded position relative to the middle portion in accordance with the present disclosure.
Figure 11D:
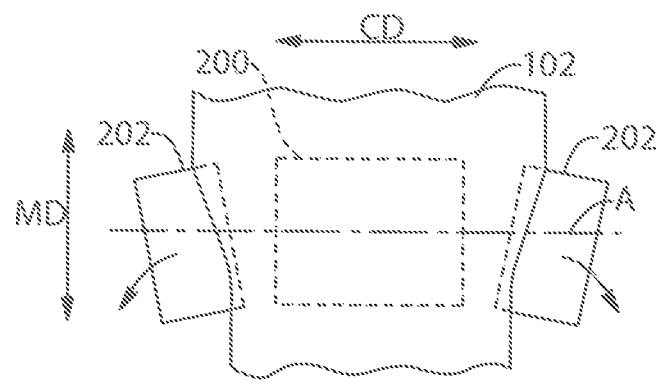
FIG. 11D is a schematic representation of a front view of the cross machine directional tensioning apparatus of FIG. 11B with the outer longitudinal portions in an angled and expanded position relative to the middle portion in accordance with the present disclosure.
Figure 11E:
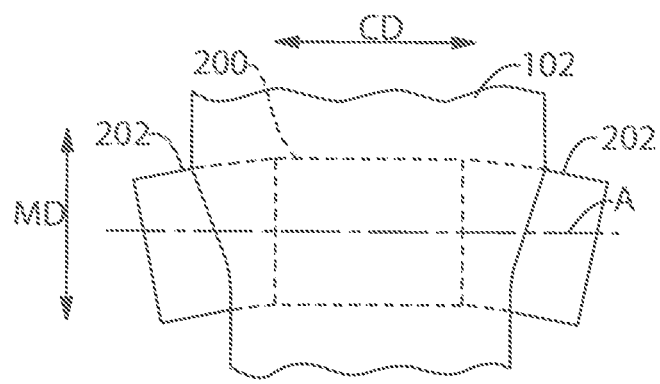
FIG. 11E is a schematic representation of a front view of a cross machine directional tensioning apparatus with outer longitudinal portions fixed in an angled position relative to a middle portion in accordance with the present disclosure.

FIG. 11B is a schematic representation of a front view of an example cross machine directional tensioning apparatus with outer longitudinal portions 202 in an unexpanded or non-angled position relative to the middle portion 200. FIG. 11C is a schematic representation of a front view of the cross machine directional tensioning apparatus of FIG. 11B with the outer longitudinal portions 202 in a longitudinally expanded position relative to the middle portion 200. FIG. 11D is a schematic representation of a front view of the cross machine directional tensioning apparatus of FIG. 11B with the outer longitudinal portions 202 in an angled and expanded position relative to the middle portion 200. In regard to FIG. 11D, the outer longitudinal portions 202 may merely move or slide in a direction generally perpendicular to the machine direction of the web passing over the roll to apply the cross machine directional tensioning force to the web 102. FIG. 11E is a schematic representation of a front view of a cross machine directional tensioning apparatus with the outer longitudinal portions 202 fixed in an angled position relative to the middle portion 200 to apply the cross machine directional tensioning force to the web 102. In such a form, the middle portion 200 and each of the outer longitudinal portions 202 may comprise a separate roll.

Regardless of whether one or both of the outer longitudinal portions 202 is moved, slid, rotated, fixed, and/or expanded relative to the middle portion 200, this relative motion or positioning between the outer longitudinal portions 202 and the middle portion 200 stretches the webs 102 in a cross machine direction to further rupture or further define the first and second weakened locations 10 and 14 in the web 102 and create a plurality of first apertures 18 in the first zone 12 and a plurality of second apertures 20 in the second zone 16 of the web 102. The cross machine directional tensioning force applied by the cross machine directional tensioning apparatus 132' may be in the ranges specified herein, such as 15 grams, for example. In one instance, the cross machine directional tensioning apparatus may be similar to, or the same as, the incremental stretching apparatus 132 to apply the cross machine directional tensioning force. In still other instances, any suitable cross machine directional tensioning apparatus may be used to apply the cross machine directional tensioning force to the web 102.

After the application of the cross machine directional tensioning force, the web width, W2, may be substantially increased, or increased, in the cross machine directional. By also optionally applying tension in the machine direction, the web width may be decreased to about the same width, W2, as it was prior to entering the cross machine directional tensioning apparatus 132'.

If desired, the incremental stretching step or the cross machine directional stretching step described herein may be performed at elevated temperatures. For example, the webs and/or the rolls may be heated. Utilizing heat in the stretching step may serve to soften the nonwoven web, and may aid in extending the fibers without breaking.

Referring again to FIG. 3, the nonwoven web 102 may be taken up on wind-up roll 180 and stored. Alternatively, the nonwoven web 102 may be fed directly into a production line where it is used to form a topsheet on an absorbent article or other portion of a consumer product or article of commerce.

Both the incremental stretching step and the applying the cross machine directional tensioning force may be done off-line or on-line. Furthermore, the incremental stretching step and the applying the cross machine directional tensioning step may be done over the entire area of the web or may be done only in certain machine direction zones of the web.

An example absorbent article that can use the web 102 discussed herein may comprise a containment assembly, commonly referred to as a "chassis" comprising a liquid pervious topsheet and a liquid impervious backsheet joined to the topsheet. An absorbent core may be positioned between the topsheet and the backsheet. The absorbent article may also comprise other components such as elasticized side panels, elasticized leg cuffs, elasticized waistbands, and a fastening system (if a taped-style absorbent article) comprising a pair of securement members (e.g., tape tabs or mechanical fastener members) and a landing zone, for example.

An absorbent article may have two centerlines, a longitudinal centerline and a transverse centerline. The term "longitudinal", as used herein, refers to a line, axis, or direction in the plane of the absorbent article that is generally aligned with (e.g., substantially parallel with) a vertical plane which bisects a standing wearer into left and right halves when the absorbent article is worn. The terms "transverse" and "lateral", as used herein, are interchangeable and refer to a line, axis or direction which lies within the plane of the absorbent article that is generally perpendicular to the longitudinal direction (which divides the wearer into front and back body halves).

The absorbent core may comprise pulp or airfelt in combination with superabsorbent polymers or may be entirely, or almost entirely, comprised of superabsorbent polymers by weight of the absorbent core.

The topsheet may be made from one or more of the nonwoven webs of the present disclosure, so as to allow viscous body fluids, like runny and pasty BM, urine, and/or menses, to penetrate the various apertures be stored in the absorbent core.

Figure 12:
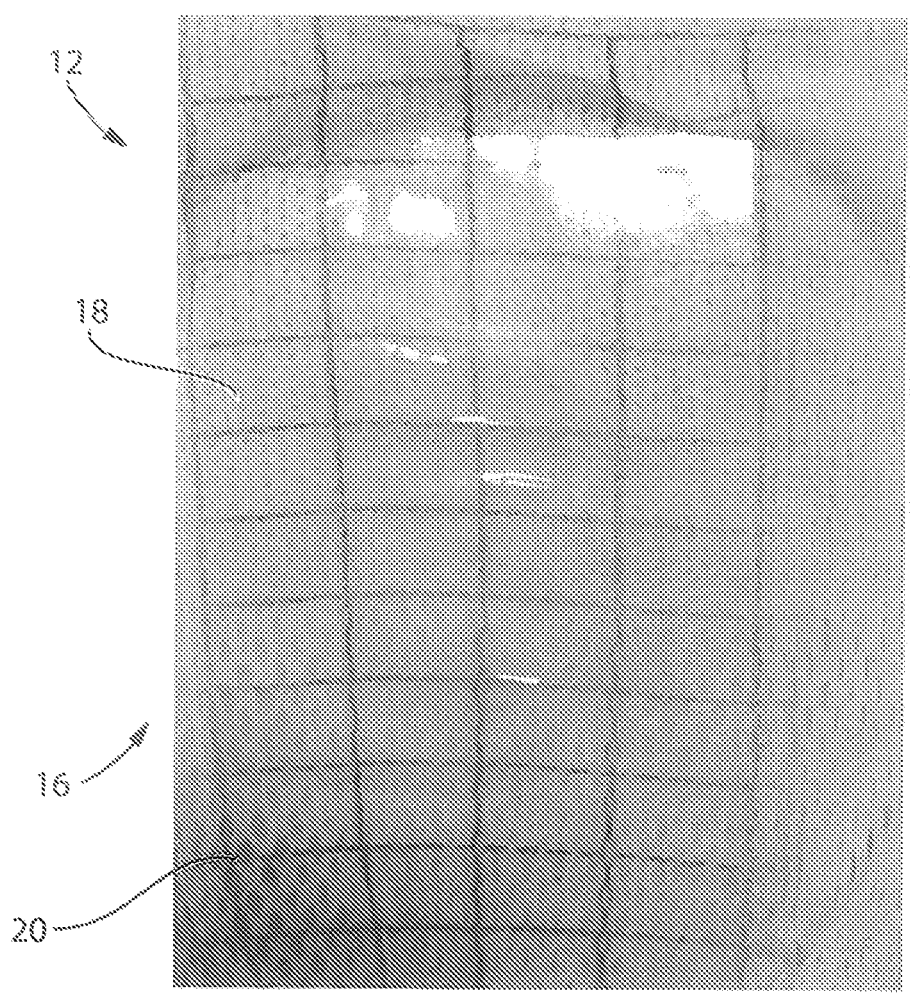
FIGS. 12 and 13 are photographs of portions of zoned apertured webs produced using the methods of the present disclosure.
Figure 13:
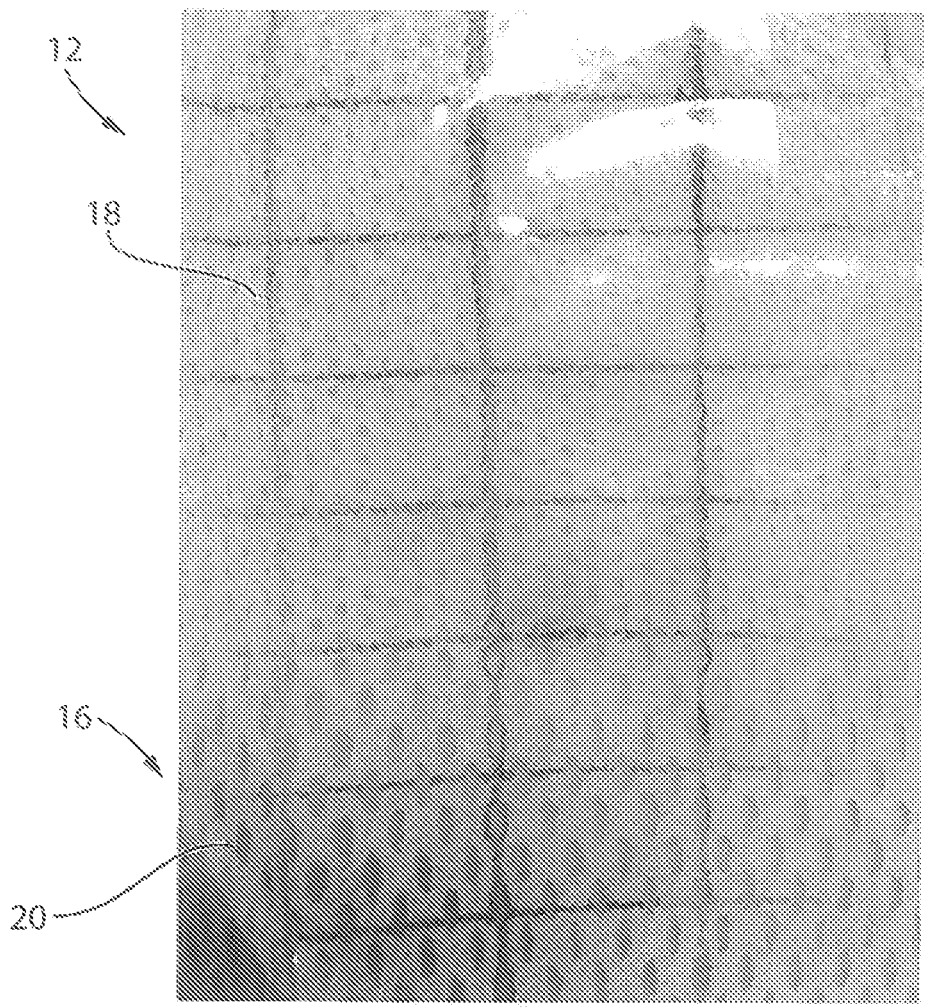

FIGS. 12 and 13 illustrate photographs of apertured nonwoven webs produced using the methods of the present disclosure. As can been seen in FIGS. 12 and 13, the apertures 18 in the first zone 12 may be smaller than the apertures 20 in the second zone 16 of the nonwoven web 102.

Figure 14:
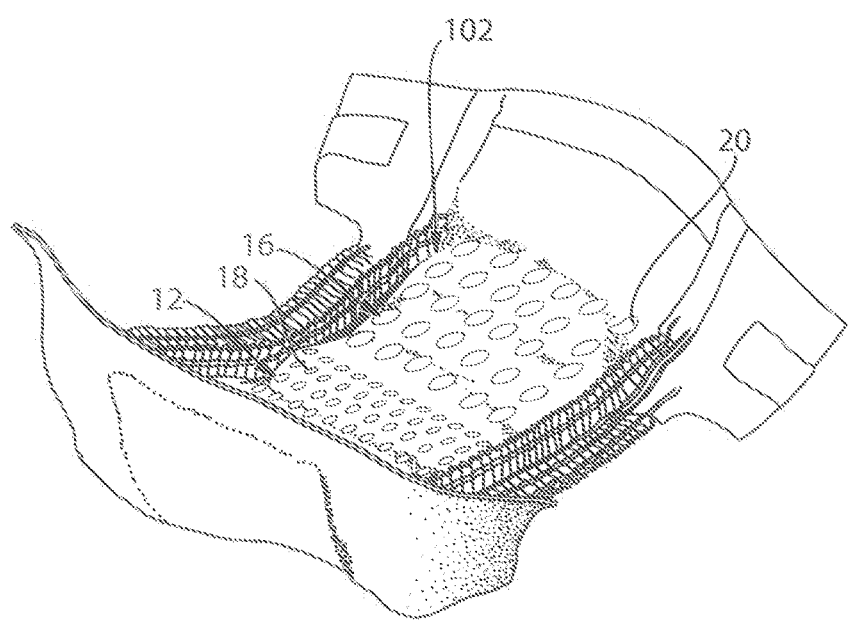
FIG. 14 is an example apertured topsheet comprising the zoned apertured webs produced using the methods of the present disclosure on an example absorbent article.

FIG. 14 illustrates an example of an apertured zoned nonwoven web 102 of the present disclosure employed as a topsheet of an absorbent article. The topsheet may have a first zone 12 having a first plurality of apertures 18 and the second zone 16 may have a second plurality of apertures 20. The apertures 18 in the first zone 12 may have a smaller effective aperture area as the apertures 20 in the second zone 16. This feature allows the apertures 18 in the first zone 12 to be configured for acquiring urine and the apertures 20 in the second zone 16 to be configured for acquiring BM or runny BM, for example.

The present disclosure also generally relates, in part, to a nonwoven web 102 comprising a first overbond pattern (e.g., elements 10 in FIG. 1) in a first zone (e.g., 12 in FIG. 1) and a second overbond pattern (e.g., elements 14 in FIG. 1) in a second zone (e.g., 16 in FIG. 1). The first overbond pattern may have elements that are the same, different, larger, smaller, wider (CD), and/or longer (MD) than the elements of the second overbond pattern. The first and second overbond patterns may be in different regions of the nonwoven web 102 (e.g., front/back of a topsheet or on opposite sides of a generally laterally extending separation element on or formed into a topsheet). The overbond patterns may be not the primary bonds used to hold the nonwoven fibers together, but instead the nonwoven web may also have primary bonds in the various zones and/or throughout the web. The nonwoven web 102, once the overbonds are at least partially ruptured, may form at least a portion of, or all of a topsheet of an absorbent article.

The present disclosure also generally relates, in part, to a nonwoven web 102 comprising a first plurality of apertures (e.g., elements 18 in FIG. 2) in a first zone (e.g., 12 in FIG. 2) and a second plurality of apertures (e.g., elements 20 in FIG. 2) in a second zone (e.g., 16 in FIG. 2). The first plurality of apertures may have a different effective aperture area as the effective aperture area as the second plurality of apertures. The apertures in each zone may also have a different CD width, MD length, shape, and/or pattern. The web 102 may have a constant, or substantially constant, cross directional width in the first zone 12 and in the second zone 16. The nonwoven web 102 may form at least a portion of, or all of, a topsheet of an absorbent article.

The present disclosure also generally relates, in part, to a nonwoven web having alternating regions in the machine direction. The regions may alternate along the machine direction as follows, a first region, a second region, the first region, the second region etc. Alternatively, there may be three or more regions that alternate along the machine direction. The first region may have a first overbond pattern and the second region may have a second, different overbond pattern. The overbond patterns may be added to the nonwoven web at a manufacturer of a final product (e.g., absorbent article manufacturer) or at the nonwoven supplier. The nonwoven web may be provided in a roll.

EXAMPLES

The substrate used to generate the data in the examples was a 28 gsm bicomponent material. The bicomponent material was a 50/50 poly-ethylene/poly-propylene core/sheath material.

| Example | Front Projection Length (MD) (mm) | Back Projection Length (MD) (mm) | Depth of Engagement of Ring Rolls | Aperture Size (mm) | | | | Aperture Area (mm^2) | | CD Web Growth from overbonded web to finished product |
|---|---|---|---|---|---|---|---|---|---|---|
| | | | | MD Length Front | CD Width Front | MD Length Back | CD width Back | Front | Back | |
| 1 | 0.05 | 0.2 | 0.050" | 1.36 | 0.75 | 4.42 | 1.49 | 0.80 | 5.17 | 5.4 mm |
| 2 | 0.15 | 0.2 | 0.050" | 3.7 | 1.02 | 4.42 | 1.49 | 2.96 | 5.17 | 5.3 mm |
| 3 | 0.05 | 0.15 | 0.060" | 1.48 | 0.91 | 3.55 | 2.03 | 1.06 | 5.66 | 7.3 mm |

Data related to CD web growth in different zones appears below. As can be seen, the CD web growth in the front zone is substantially the same as the CD web growth in the back zone.

| | Front Zone CD Web Growth | Back Zone CD Web Growth | Delta (mm) CD Web Growth |
|---|---|---|---|
| Example 1 | 5.3 | 5.8 | 0.5 |
| Example 2 | 5.3 | 5.8 | 0.5 |
| Example 3 | 5.3 | 5.3 | 0 |

This substantial similarity of the CD web growth of the front and back zones allows for better processing of the web, owing to its substantially uniform CD width.

Methods
Aperture Test

Aperture dimensions, effective aperture areas, and % effective open area measurements are performed on images generated using a flat bed scanner capable of scanning in reflectance mode at a resolution of 6400 dpi and 8 bit grayscale (a suitable scanner is the Epson Perfection V750 Pro, Epson, USA). Analyses are performed using ImageJ software (v.s 1.46, National Institute of Health, USA) and calibrated against a ruler certified by NIST. A steel frame (100 mm square, 1.5 mm thick with an opening 60 mm square) is used to mount the specimen and a black glass tile (P/N 11-0050-30, available from HunterLab, Reston, Va.) is used as the background for the scanned images. Testing is performed at about 23° C.±2° C. and about 50%±2% relative humidity.

Take the steel frame and place double-sided adhesive tape on the bottom surface surrounding the interior opening. To obtain a specimen, lay the article flat on a bench with the body-facing surface directed upward. Visually inspect the article's topsheet for zones that have apertures of visually different dimensions (e.g., the front half and the back half of the topsheet). Select the site for analysis such that the frame will enclose a zone where the apertures are substantially the same dimension. Remove the release paper of the tape, and adhere the steel frame to the topsheet of the article. Using a razor blade excise the topsheet from the underling layers of the article around the outer perimeter of the frame. Carefully remove the specimen such that its longitudinal and lateral extension is maintained. A cryogenic spray (such as Cyto-Freeze, Control Company, Houston Tex.) may be used to remove the top sheet specimen from the underling layers, if necessary. Five replicates obtained from five substantially similar articles at the corresponding site on each are prepared for analysis. Condition the samples at about 23° C.±2° C. and about 50%±2% relative humidity for 2 hours prior to testing.

Place the ruler on the scanner bed, close the lid and acquire a 50 mm by 50 mm calibration image of the ruler in reflectance mode at a resolution of 6400 dpi and 8 bit grayscale. Save the image as an uncompressed TIFF format file. Lift the lid and remove the ruler. After obtaining the calibration image, all specimens are scanned under the same conditions and measured based on the same calibration file. Next, place the framed specimen onto the center of the scanner bed with the body-facing surface of the specimen facing the scanner's glass surface. Place the black glass tile on top of the frame covering the specimen, close the lid and acquire a scanned image. In like fashion, scan the remaining four replicates.

Open the calibration file in ImageJ and perform a linear calibration using the imaged ruler, with the scale set to Global so that the calibration will be applied to subsequent specimens. Open a specimen image in ImageJ. View the histogram and identify the gray level value for the minimum population located between the dark pixel peak of the holes and the lighter pixel peak of the nonwoven. Threshold the image at the minimum gray level value to generate a binary image. In the processed image, the apertures appear as black and nonwoven as white.

Select the analyze particles function. Set the minimum aperture area exclusion limit to 0.3 mm$^2$ and for the analysis to exclude the edge apertures. Set the software to calculate: effective aperture area, perimeter, feret (MD length of the aperture) and minimum feret (CD width of the aperture). Record the effective aperture area to the nearest 0.01 mm$^2$, and the average perimeter, to the nearest 0.01 mm. Again select the analyze particles function, but his time set the analysis to include the edge holes as it calculates the effective aperture areas. Sum the effective aperture areas (includes whole and partial apertures) and divide by the total area included in the image (2500 mm$^2$) Record as the % effective open area to the nearest 0.01%

In like fashion analyze the remaining four specimen images. Calculate and report the effective aperture area to the nearest 0.01 mm$^2$, the average aperture perimeter, the feret and the minimum feret to the nearest 0.01 mm, and the % effective open area to the nearest 0.01% for the five replicates.

This test is repeated for each of the visually identified aperture regions within the topsheet.

Basis Weight Test

Basis weights of the visually different zones of the topsheets may be determined by several available techniques, but a simple representative technique involves taking a diaper or other absorbent article, removing any elastic which may be present and stretching the diaper or absorbent product to its full length. A punch die having an area of 45.6 cm² is then used to cut a piece of topsheet in each of the visually different zones of the diaper or absorbent product in locations which avoid, to the greatest extent possible, any adhesive which may be used to fasten the topsheet to any other layers which may be present and removing the topsheet layer from other layers (using cryogenic spray, such as Cyto-Freeze, Control Company, Houston, Tex., if needed). Each of the samples from the two visually different zones are then weighed. Dividing the weight of each sample by the area the punch die results in the basis weight of the topsheet in each of the visually different zones. Results are reported as a mean of 5 samples for each of the visually different zones.

Measuring the Substantially Constant Cross Directional Width

Condition the samples at about 23° C.±2° C. and about 50%±2% relative humidity for 2 hours prior to testing.

Open the absorbent article and place it on a lab bench with the topsheet facing upward. Stretch the absorbent article flat, and using masking tape, secure it to the bench. Measure and record the total longitudinal length of the absorbent article. Measure down, starting from the front waist, a distance one third of the total length of the absorbent article, and mark a site at the longitudinal centerline of the absorbent article. Repeat for the back waist. Identify where the topsheet is bonded to the inner cuff. Using a calibrated ruler (accurate to ±1 mm and traceable to NIST or other standards organization) measure the lateral distance (CD), perpendicular to the longitudinal centerline of the absorbent article, from the left inner cuff/topsheet bond to the right inner cuff/topsheet bond at the two marked sites. Record the distances as the topsheet front CD width and the topsheet back CD width to the nearest 1 mm. Repeat for a total of five substantially similar absorbent articles, and report as the average value to the nearest 1 mm. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure.

It is therefore intended to cover in the appended claims all such changes and modifications that are within the scope of this disclosure.

What is claimed is:

1. A method for making a zoned apertured nonwoven web, the method comprising:
    advancing a nonwoven web in a machine direction;
    overbonding the nonwoven web at a plurality of first locations in a first zone of the nonwoven web to create a first plurality of overbonds that are situated in a first pattern, wherein the first plurality of overbonds are substantially the same size;
    overbonding the nonwoven web at a plurality of second locations in a second zone of the nonwoven web to create a second plurality of overbonds that are situated in a second pattern that is different than the first pattern, wherein the second plurality of overbonds are substantially the same size, wherein the first zone is positioned further upstream than the second zone relative to the machine direction;
    wherein the first plurality of overbonds are free of overlap with the second plurality of overbonds in a cross machine direction, and wherein the nonwoven web remains unapertured;
    incrementally stretching the nonwoven web to locally extend portions of the nonwoven web in a direction substantially parallel to a cross machine direction to cause the nonwoven web to rupture at some of the first and second pluralities of overbonds in the first and second zones; and
    applying a substantially cross machine directional tensioning force to the nonwoven web to cause the nonwoven web to further rupture at the some of the first and second pluralities of overbonds in the first and second zones to create:
        a plurality of first apertures in the nonwoven web coincident with the some of the first plurality of overbonds in the first zone; and
        a plurality of second apertures in the nonwoven web coincident with the some of the second plurality of overbonds in the second zone;
    wherein a cross machine directional width of the nonwoven web after the applying step is substantially the same in the first zone and the second zone, and wherein any cross machine directional line taken in the nonwoven web only intersects the first zone or only intersects the second zone.

2. The method of claim 1, wherein the apertures in the first zone are different in effective aperture area than the apertures in the second zone, and wherein the first zone is free of overlap with the second zone in the cross machine direction.

3. The method of claim 1, wherein the first pattern extends across a cross machine direction of the nonwoven web, and wherein the second pattern extends across the cross machine direction of the nonwoven web.

4. The method of claim 1, wherein the cross machine directional width of the nonwoven web in the first zone is within 2 mm of the cross machine directional width of the nonwoven web in the second zone after applying step.

5. The method of claim 1, wherein the overbonding step comprises overbonding the nonwoven web with an overbonding roll having a first pattern of radially outwardly extending protrusions positioned on a radial outer surface of the overbonding roll and a second pattern of radially outwardly extending protrusions positioned on the radial outer surface of the overbonding roll.

6. The method of claim 5, wherein the first pattern of radially outwardly extending protrusions extends around about 50% of a circumference of the overbonding roll in the direction of rotation of the roll, and wherein the second pattern of radially outwardly extending protrusions extends around about 50% of the circumference of the overbonding roll in the direction of rotation of the roll, and comprising using the overbonding roll to form a cross machine directionally extending boundary zone in the nonwoven web intermediate the first zone and the second zone.

7. The method of claim 5, wherein the first pattern of radially outwardly extending protrusions extends around less than 50% of a circumference of the overbonding roll in the direction of rotation of the roll.

8. The method of claim 1, comprising advancing the nonwoven web through a nip during the overbonding.

9. The method of claim 1, wherein the overbonding steps comprise applying heat or pressure to the nonwoven web.

10. The method of claim 1, wherein the cross machine directional tensioning force is in the range of about 13 grams to about 17 grams.

11. The method of claim 1, wherein the incremental stretching is substantially constant in the first zone and the second zone.

12. A method for making a zoned apertured nonwoven web, the method comprising:
   providing an unapertured nonwoven web comprising:
      a first plurality of overbonds that are situated in a first pattern in a first zone, wherein the first plurality of the overbonds are substantially the same size; and
      a second plurality of overbonds that are situated in a second, different pattern in a second zone, wherein the second plurality of overbonds are substantially the same;
      wherein the first plurality of overbonds are free of overlap with the second plurality of overbonds in a cross-machine direction;
   advancing the nonwoven web in a machine direction such that the first zone is positioned further upstream relative to the second zone in the machine direction, wherein a boundary is present intermediate the first zone and the second zone, and wherein the boundary extends in a cross machine direction;
   incrementally stretching the nonwoven web to locally extend portions of the nonwoven web in a direction substantially parallel to a cross machine direction to cause the nonwoven web to rupture at some of the first and second pluralities of overbonds in the first and second zones; and
   applying a substantially cross machine directional tensioning force to the nonwoven web to cause the nonwoven web to further rupture at the some of the first and second pluralities of overbonds in the first and second zones to create:
      a plurality of first apertures in the nonwoven web coincident with the some of the first plurality of overbonds in the first zone; and
      a plurality of second apertures in the nonwoven web coincident with the some of the second plurality of overbonds in the second zone;
   wherein the cross machine directional width of the nonwoven web after the applying step is substantially the same in the first zone and the second zone.

13. The method of claim 12, wherein the apertures in the first zone are different in effective aperture area than the apertures in the second zone, and wherein the first zone is free of overlap with the second zone in the cross machine direction.

14. The method of claim 12, wherein the first pattern extends fully across the cross machine direction of the nonwoven web, and wherein the second pattern extends fully across the cross machine direction of the nonwoven web.

15. The method of claim 12, wherein the first and second plurality of overbonds are formed by overbonding the unapertured nonwoven web.

16. A method for making a zoned apertured nonwoven web, the method comprising:
   providing an unapertured nonwoven web comprising:
      a first plurality of overbonds that are situated in a first pattern in a first zone, wherein the first plurality of overbonds are substantially the same size; and
      a second plurality of overbonds that are situated in a second, different pattern in a second zone, wherein the second plurality of overbonds are substantially the same size;
      wherein the first plurality of overbonds are free of overlap with the second plurality of overbonds in a cross machine direction;
   advancing the nonwoven web in a machine direction such that the first zone is positioned further upstream than the second zone relative to the machine direction, wherein the first zone is separated from the second zone by a cross machine directional boundary; and
   applying a substantially cross machine directional tensioning force to the nonwoven web to cause the nonwoven web to rupture at some of the first and second pluralities of overbonds in the first and second zones to create:
      a plurality of first apertures in the nonwoven web coincident with the some of the first plurality of overbonds in the first zone; and
      a plurality of second apertures in the nonwoven web coincident with the some of the second plurality of overbonds in the second zone, wherein the plurality of first apertures each have an effective aperture area that is different than an effective aperture area of the plurality of second apertures.

17. The method of claim 16, comprising incrementally stretching the nonwoven web prior to the applying step to locally extend portions of the nonwoven web in a direction substantially parallel to the cross machine direction.

18. The method of claim 16, wherein the cross machine directional width of the nonwoven web after the applying step is substantially the same in the first zone and the second zone.

* * * * *